United States Patent

Murray

[11] 3,981,299
[45] Sept. 21, 1976

[54] URETHRAL CATHETER

[76] Inventor: Harry Elmer Murray, 412 E. Pierce, Kirksville, Mo. 63501

[22] Filed: Mar. 15, 1971

[21] Appl. No.: 603,371

[52] U.S. Cl. ............................ 128/349 B; 128/260
[51] Int. Cl.² ........................................ A61M 25/00
[58] Field of Search ............ 128/348, 349 R, 349 B, 128/349 BV, 350 R, 351, 344, 260

[56] References Cited
UNITED STATES PATENTS

| | | | |
|---|---|---|---|
| 1,596,754 | 8/1926 | Moschelle | 128/350 R |
| 2,548,602 | 4/1951 | Greenburg | 128/344 X |
| 3,173,418 | 3/1965 | Baran | 128/351 |
| 3,348,542 | 10/1967 | Jackson | 128/260 X |
| 3,394,705 | 7/1968 | Abramson | 128/349 B |
| 3,593,713 | 7/1971 | Bogott et al. | 128/349 B |

*Primary Examiner*—Dalton L. Truluck
*Attorney, Agent, or Firm*—D. Paul Weaver

[57] ABSTRACT

A urethral catheter construction having a third tubular extension or finger which will permit injections of antibiotics or an anesthetic onto the outer wall of the catheter through a very thin porous rubber outer membrane.

2 Claims, 6 Drawing Figures

URETHRAL CATHETER

This invention relates to a surgical appliance, and more particularly to an improved urethral catheter.

It is therefore the primary object of this invention to provide a catheter structure which will have a third finger for permitting injections of antibiotics or an anesthetic onto the outer wall of the catheter via a very thin rubber outer membrane, the membrane being highly porous and permeable.

Another object of this invention is to provide a catheter construction which will have a plurality of minute rubber elevations between the outer membrane and the underlying catheter body so as to prevent possible ballooning of the membrane when injecting any type of medication into the thin outer membrane.

A further object of this invention is to provide an improved catheter which will have rubber projections or elevations arranged in alternating rows permitting the injected medication to infiltrate the porous openings of the outer membrane, thus enveloping the catheter, spreading the medicant between the outer wall of the catheter and the urethral mucosa.

Due to the inherent structure of this invention, it will be readily conceived that any infection which might be introduced by the mechanical process of catheterization can be more readily dealt with by the introduction of antibiotics prophylacticly.

It shall also be recognized that since catheterization can be a traumatic experience for some individuals, the use of sol or gel types of anesthetics can be used as a lubricant for the introduction of the catheter on or immediately after introduction, making catheterization more tolerable.

Since the sphincters in this area are under the control of the central nervous system, they will not be affected by this type of medication, however, the mucosal lining of the urethal tract will be affected, which is the purpose of this type of medication.

It shall further be recognized that the crust formation on the outer wall of the catheter due to the prostatic or urethral mucosal secretion can be greatly reduced and readily cleared on routine irrigations, thus preventing irritation, and infections. In subsequent care of the catheterized patient, repeated injections of medication, anesthetics or simple irrigations of the urethral passage may be performed through the catheter with a minimum disturbance of the patient.

Other features and advantages of the invention will become apparent during the course of the following detailed description.

BRIEF DESCRIPTION OF DRAWING FIGURES

Figure 2:
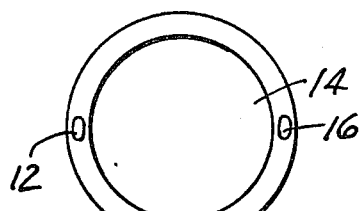
FIG. 2 is an enlarged transverse section taken along the lines 2—2 of FIG. 1.
Figure 3:
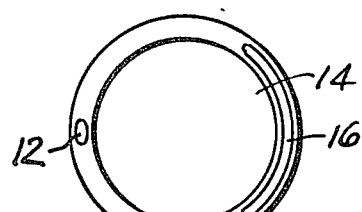
FIG. 3 is an enlarged transverse section taken along the line 3—3 of FIG. 1.
Figure 4:
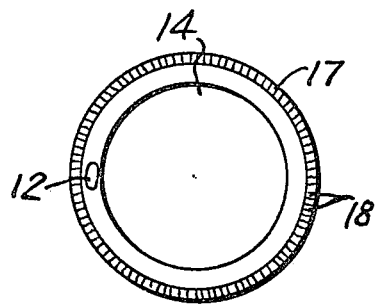
FIG. 4 is an enlarged transverse section taken along the line 4—4 of FIG. 1.

According to this invention, a urethral catheter 10 is shown to include a conventional finger or extension 11 having an opening 12 for inflation in a manner well known in the art.

A central conventional finger 13 includes an opening 14 for bladder drainage in the usual manner. A third finger 15 comprising an element of the invention includes an opening 16 for the introduction of medication, anesthetics or irrigating solutions.

The catheter 10 also includes a thin outer membrane 17, intermediate its ends beneath which are a plurality of minute rubber projections 18. Membrane 17 is provided with a plurality of pores or openings 19, as shown.

The catheter 10 further includes a conventional inflatable bulb 20 spaced from the usual bladder drainage openings 21 and the porous membrane 17. This inflatable bulb communicates with the opening 12 of extension 11. Similarly, the interior of porous membrane 17 communicates with the opening or port 16 of extension 15.

Figure 5:
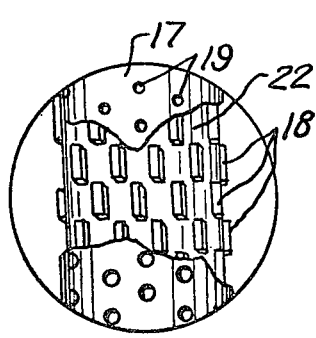
FIG. 5 is an enlarged and fragmentary elevational view of the body and membrane of the present invention.
Figure 6:
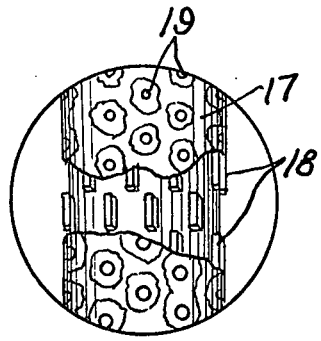
FIG. 6 is an enlarged fragmentary view similar to FIG. 5, but showing the medication flow.
Figure 1:
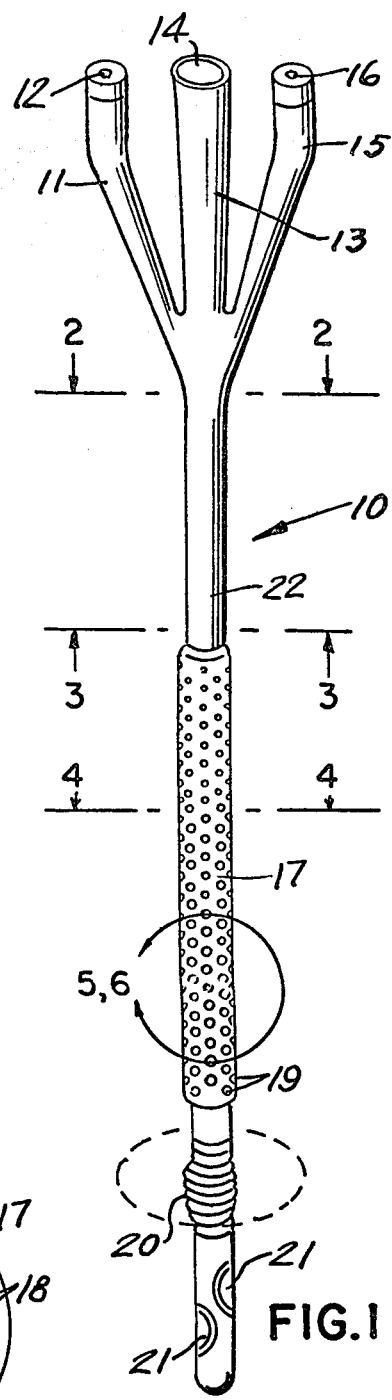
FIG. 1 is a perspective view of the present invention.

The elements 18 are formed on the exterior of the catheter body 22 as best shown in FIGS. 5 and 6 and the membrane 17 overlies these elements or projections and is spaced thereby from the body 22.

In use, the injection of any type of medication into such a thin member 17 is likely to produce a ballooning of membrane 17, however, this problem is overcome by the spaced apart rubber projections 18 between the outer membrane 17 and the underlying catheter body 22.

The rubber projections 18 are so arranged in alternating rows so as to permit the injected medication to infiltrate through the porous openings 19 of the outer membrane 17, thus allowing spreading of the medicant between the outer wall of the catheter 10 and the urethral mucosa, see FIG. 6.

I claim:

1. A urethral catheter comprising an elongated body portion having drainage openings near one end thereof and a drainage tube extension at its opposite end, an inflatable element on said body portion in spaced relation to said drainage openings, a coacting inflation means for said inflatable element on the body portion near said opposite end, a porous thin flexible outer membrane sleeve on and surrounding the body portion over a substantial portion of its length and spaced from said inflatable element and having opposite end portions joined to said body portion, said thin membrane sleeve tending to collapse against the exterior of the body portion due to confining pressure when the catheter is inserted into a body cavity, a multiplicity of spaced relatively small uniform height and substantially equally sized fixed projections on the exterior of the body portion and lying beneath the membrane sleeve and serving to maintain the latter spaced from the exterior of the body portion over substantially the full area of the sleeve and preventing collapse of the membrane sleeve inwardly against the body portion, and fluid conduit means on the body portion near said opposite end and communicating with the interior of the membrane sleeve, whereby fluids may be introduced into the membrane sleeve for treatment of the urethral canal while the catheter is implanted therein.

2. A urethral catheter as defined in claim 1 and said projections being arranged on the body portion in alternating circumferentially staggered rows and each being a small block-like element which is somewhat elongated on the major longitudinal axis of the catheter, the arrangement of the projections permitting free circulation of liquid medicaments within and through the porous membrane sleeve while preventing collapsing of the membrane sleeve on the body portion.

* * * * *